(12) United States Patent
Hunicke-Smith et al.

(10) Patent No.: US 6,387,031 B1
(45) Date of Patent: May 14, 2002

(54) ARRAY CENTRIFUGE

(75) Inventors: Scott P. Hunicke-Smith, Menlo Park; Carl Buice, Mountain View; Benjamin Riepe, San Mateo; Theodore Rogers, Berkeley, all of CA (US)

(73) Assignee: Genomic Instrumentation Services, Inc., San Carlos, CA (US)

( * ) Notice: Subject to any disclaimer, the term of this patent is extended or adjusted under 35 U.S.C. 154(b) by 0 days.

(21) Appl. No.: 09/494,132

(22) Filed: Jan. 28, 2000

Related U.S. Application Data

(60) Provisional application No. 60/118,013, filed on Jan. 29, 1999.

(51) Int. Cl.[7] .............................. B04B 5/10; B04B 9/00
(52) U.S. Cl. ........................................... 494/31; 494/84
(58) Field of Search .............................. 494/16, 19, 31, 494/33, 83, 84; 422/72

(56) References Cited

U.S. PATENT DOCUMENTS

| | | | |
|---|---|---|---|
| 442,461 A | 12/1890 | Sharples | |
| 556,567 A | 3/1896 | Waring | |
| 731,215 A | 6/1903 | Patterson | |
| 749,104 A | 1/1904 | Schoenefeldt | |
| 773,220 A | 10/1904 | Patterson | |
| 901,056 A | 10/1908 | Atkins et al. | |
| 1,111,600 A | 9/1914 | Mauss | |
| 1,630,412 A | 5/1927 | Wescott | |
| 2,340,825 A | 2/1944 | Stern | |
| 2,822,127 A | 2/1958 | Sinn | |
| 2,875,949 A | 3/1959 | Tarsoly | |
| 3,722,790 A | 3/1973 | Natelson | |
| 3,944,133 A | * 3/1976 | Kesell et al. | |
| 4,262,840 A | 4/1981 | Gronert et al. | |
| 4,286,748 A | 9/1981 | Bailey | |
| 4,289,270 A | 9/1981 | Warsinke | |
| 4,305,546 A | 12/1981 | Gropper | |
| 5,222,933 A | 6/1993 | Knelson et al. | |
| 5,380,087 A | 1/1995 | Haber et al. | |
| 5,505,684 A | 4/1996 | Piramoon | |
| 5,840,005 A | 11/1998 | Lowe et al. | |
| 6,238,330 B1 | * 5/2001 | Marziali | ...................... 494/31 |

FOREIGN PATENT DOCUMENTS

| | | | |
|---|---|---|---|
| WO | WO97/18022 | 5/1997 | |
| WO | 99/12651 | * 3/1999 | .................. 494/31 |

* cited by examiner

Primary Examiner—Charles E. Cooley
(74) Attorney, Agent, or Firm—Seed Intellectual Property Law Group PLLC

(57) ABSTRACT

The present invention is directed to a microcentrifuge apparatus adapted to simultaneously spin a plurality of samples contained within a plurality of rotors. The microcentrifuge comprises an upper plate that has a plurality of upper plate holes; and a lower plate that has a plurality of lower plate holes or recesses. The lower plate is adjacent and substantially parallel to the upper plate, and the plurality of lower plate holes or recesses are in axial alignment with the plurality of upper plate holes. The plurality of rotors are adapted for retaining and spinning the plurality of samples, and are positioned between the upper plate and the lower plate. Each of the plurality of rotors has at opposing ends an upper shaft and a lower shaft, wherein the upper shaft engages one of the upper plate holes and the lower shaft engages one of the lower plate holes or recesses such that the axes of rotation of each of the plurality rotors are substantially perpendicular to the upper and lower plates. In addition, each of the rotors has a central outer surface portion positioned between the upper and lower plates, wherein the central outer surface portion is outwardly bulged. The microcentrifuge further comprises a pulley and a drive belt that is operatively engaged with the pulley and the bulged central outer surface portion of each of the plurality of rotors.

4 Claims, 11 Drawing Sheets

ARRAY CENTRIFUGE

This application claims the benefit of U. S. Provisional Application No. 60/118,013, filed Jan. 29, 1999.

STATEMENT OF GOVERNMENT INTEREST

This invention was made with government support under Grant Nos. HG02125-01 and HG02125-02 awarded by The National Human Genome Research Institute. The government may have certain rights in this invention.

TECHNICAL FIELD

This invention relates generally to microcentrifugation instruments and techniques, specifically to an improved arrayable microcentrifuge for simultaneous centrifugation of samples.

BACKGROUND OF THE INVENTION

Centrifugation as a means of accelerating sedimentation of precipitates and particulates has long been an integral part of biochemical protocols. A typical centrifuge consists of a rotor encased in a housing. The rotor is powered by a drive motor or some other force that allows it to complete a set number of rotations per minute (rpm). Attached to the rotor are holders in which to place sample containers, such as test tubes or well plates. These holders are placed symmetrically around the circumference of the rotor. The sample containers are balanced to insure a symmetric mass distribution around the rotor. The sample containers are placed in the holders and the samples can then be spun and separated.

Separation of the samples occurs because each component has a different density and thus a different sedimentation velocity. Sedimentation velocity is a measure of how fast a component will migrate through other more buoyant sample components as a result of the centrifugal field generated by the centrifuge.

Using centrifugation, a variety of samples can be separated. Specific types of cell organelles can be isolated, particles can be removed from a suspension, and different liquids in a solution can be separated. The amount of separation of a sample is determined by the rpm used and the length of time the sample is spun. Recently, the increasing demand for high-throughput assays in the field of biochemistry has created a need for parallel processing and automation of many such protocols. Standard centrifuges have proven to be incompatible with these needs.

The need for highly parallel sample processing has led the science community to usage of multiwell plates. Because of the plates' insufficient mechanical strength, centrifugation of samples held in such plates is limited to accelerations below 3,500×g. Furthermore, multiwell plate centrifuges are large and cumbersome to automate. Though automation of centrifuge-based sample preparation has been performed (AutoGen 740, AutoGen, Framingham, Mass.), the resulting instruments have limits (<96 samples/hr per instrument) as a result of these difficulties.

Filter-based separation protocols also have been automated by several companies (Qiagen, Chatsworth, Calif., and Beckman Coulter, Palo Alto, Calif) but also are limited in throughput (roughly 96 samples/hr per instrument) and are at least 10 times more expensive than centrifuge-based separations.

The main limitations of centrifuges are 1) the need for a large amount of manual labor to load and unload them, 2) the small number of samples that can be spun down at one time, and 3) the length of time it takes to spin down samples. In addition, the maximum acceleration used in current centrifuges is limited by the mechanical strength of the sample containers, particularly multi-well plates, which increases the amount of time needed to spin down samples. Although these problems could be overcome by the use of robotic arms and the purchase of more centrifuges, the cost and space requirements would be prohibitive for most laboratories.

PCT Application No. PCT/US98/18930 (published as International Publication No. WO 99/12651) addresses some of these problems by disclosing a high-throughput centrifugation system in which samples are spun directly in contact with individual, miniature rotors rather than a sample holder. However, this system does not disclose an efficient means for the simultaneous rotation and restraint of the rotors. Moreover, this application does not disclose an efficient means for containing samples and protecting the apparatus from spillage. What is needed is a reliable and efficient high-throughput automated centrifugation apparatus.

SUMMARY OF THE INVENTION

In one embodiment, a microcentrifuge apparatus has a plurality of rotors for simultaneously spinning a plurality of samples; a retainer for retaining each of the rotors on a bearing surface; and at least one source of motive power (i.e., a motor), coupled to the rotors by a coupling means, for causing each of the rotors to spin at substantially the same rate. The coupling means is preferably a drive belt such as a single continuous drive belt.

In another embodiment, the microcentrifuge apparatus has a plurality of rotors for spinning a plurality of samples; a retainer for retaining each of the rotors on a bearing surface; at least one source of motive power for spinning the rotors; and at least one drive belt, coupled between the power source and each of the rotors, for applying the motive power to each of the rotors.

In another embodiment, the microcentrifuge has a plurality of rotors, each having a longitudinal axis and each containing a sample, a plurality of retainers for retaining each rotor at its predetermined location; a bearing surface located at each predetermined location for supporting each rotor as it is spun; and a source of rotating power coupled to the rotors for spinning each rotor on its longitudinal axis.

In another embodiment, the micro-array centrifuge has the following: a. a lower plate with a plurality of recesses; b. an upper plate with a plurality of holes, each hole lined by a raised cuff; c. a plurality of rotors, each having a longitudinal axis, top, bottom, crown, side and upper shaft, the side and crown maintaining contact with a drive belt; d. a motor for moving the drive belt, which in turn spins the rotors about their longitudinal axes; e. a cap with an inner and an outer lip, the inner lip adhering to the upper shaft and the outer lip being outside of the raised cuff and in close proximity to the top surface of the top plate, whereby fluid is prevented from getting into the microarray centrifuge; and f. each rotor bottom contacting at least one bearing which contacts at least one recess in the lower plate.

In another embodiment, the microcentrifuge has a lower plate divided into strips, each of which is anchored at its end.

In another embodiment, the microcentrifuge has a plurality of disposable rotors for simultaneously spinning a plurality of samples, a retainer for retaining each of the rotors on a bearing surface; and a source of motive power, coupled to the rotors, for spinning each of the rotors at substantially the same rate. The disposable rotors fit into and are removable Prom a plurality of rotor encasements of the array centrifuge. The disposable rotors comprise one or more chambers for samples.

DETAILED DESCRIPTION OF THE INVENTION

One of the best ways to address the need for highly parallel sample processing in the field of biotechnology is a high-throughput centrifugation system in which samples are spun directly in contact with individual, miniature rotors rather than with a sample holder. One such system is disclosed in PCT Application No. PCT/US98/18930 (published as International Publication No. WO 99/12651). The application discloses the preferred embodiment of using a fluid stream to spin the rotors on their longitudinal axis, wherein the transferring momentum comprises a set of indentations in an exterior surface of each rotor. However, due to variable bearing friction, it is difficult to obtain uniformity of rotation rates from rotor to rotor especially over a wide range of velocities using a high velocity fluid stream as a means of driving the rotors. This difficulty arises due to the variation of the friction from bearing to bearing in the ball bearings used to retain the rotors and results in widely varying steady state rotational velocities of the rotors.

The present invention discloses an improved high-thoroughput, automated centrifuge. Similar to the invention disclosed above, it is a centrifuge in which samples are spun directly in contact with individual, miniature rotors rather than with a sample holder. However, instead of powering the rotors with a fluid stream, the present invention discloses a source of motive power, such as a motor, coupled to the rotors by various mechanical coupling means. This configuration provides for precise, uniform rotational velocity of the rotors across the entire array of rotors for a wide range of velocities and helps keep the rotors in place. The invention further discloses a means of restraining the rotors using lubricated bearings and a bearing surface. Another advantage is the addition of a resilient ring between the lubricated bearings and the bearing surface for providing consistent pre-load for the bearings as well as noise reduction.

Figure 1:
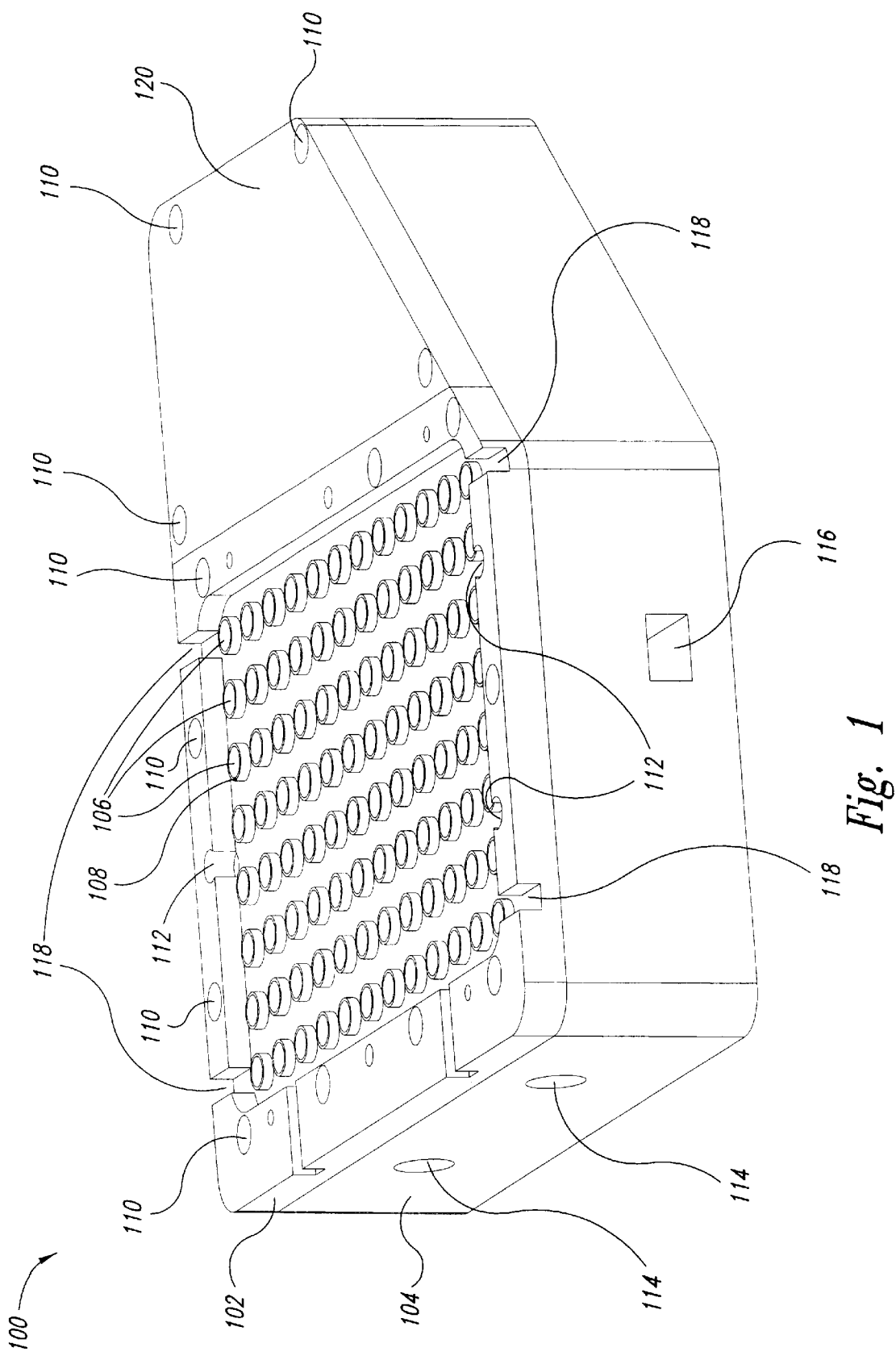
FIG. 1 is an overview of a microcentrifuge.

In FIG. 1, an exemplary microcentrifuge 100 has an upper plate 102 and a lower plate 104, both of which enclose a plurality of rotors (not shown). A preferred material for the upper and lower plates 102, 104 is aluminum. The lower plate 104 may have a solid bottom, or it may have holes (not shown) under any and all the rotors (not shown) and their respective bearings (not shown). The upper plate 102 has a plurality of holes 106 surrounded by raised cuffs 108, which in turn surround the rotors (not shown). The upper plate 102 is connected to the lower plate 104 by a plurality of screws (not shown) located on the periphery of the upper plate 102 within a plurality of screw holes 110. The upper plate 102 also has a plurality of instrument alignment holes 112 to accommodate alignment pins (not shown) associated with other instruments, such as for example a pipetter used for dispensing and aspirating samples into the rotors (not shown). An air inlet hole 114 lets in air for passive cooling; for more effective cooling or heating, a tube (not shown) may be attached to a fitting (not shown) at the air inlet hole 114 such that heated or cooled air may be delivered to the microcentrifuge 100. An open slot 116 may be used for a speed sensor (not shown) that monitors the rotational rate of the rotors (not shown) and ensures that the rotors are moving at the correct rate. A plurality of drainage slots 118 are located on the upper plate 102 allow for drainage if there is spillage of the samples. FIG. 1 also illustrates a pulley cover plate 120 that covers a pulley (not shown) and protects it from outside elements. The pulley cover plate 120 is preferably made out of a machinable metal, such as anodized aluminum.

Figure 2:
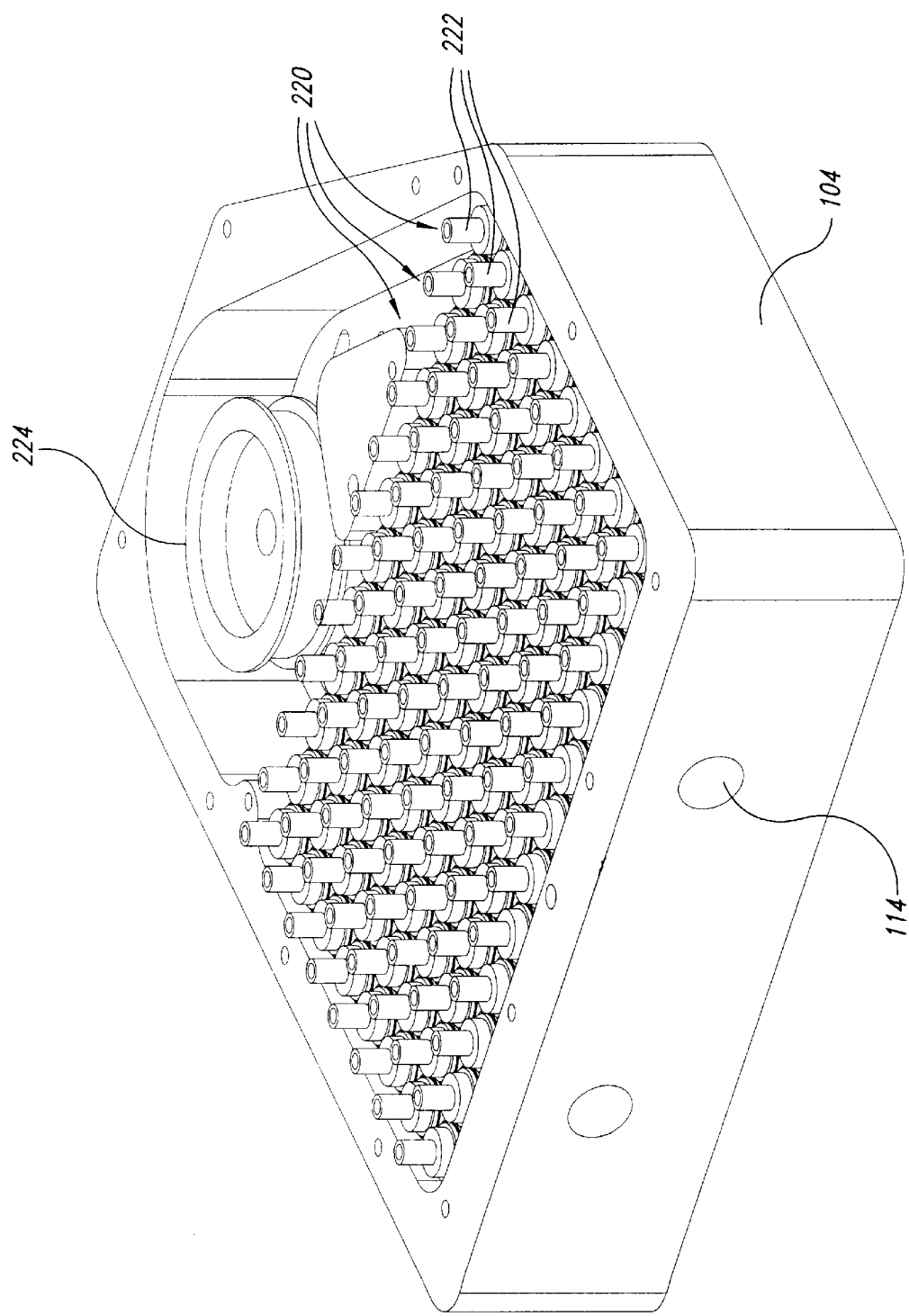
FIG. 2 is an overview of the microcentrifuge after the cover has been removed.

FIG. 2 shows the microcentrifuge 100 of FIG. 1, but with the upper and pulley cover plates 102, 120 removed thereby showing the placement of the plurality of rotors 220. As shown, each of the plurality of rotors 220 has an upwardly protruding shaft portion 222. Also shown is the pulley 224 that is driven by a DC motor (not shown). A controller (not shown) connects the motor and a remote computer (not shown), which determines when and how fast the rotors 220 will spin.

Figure 3:
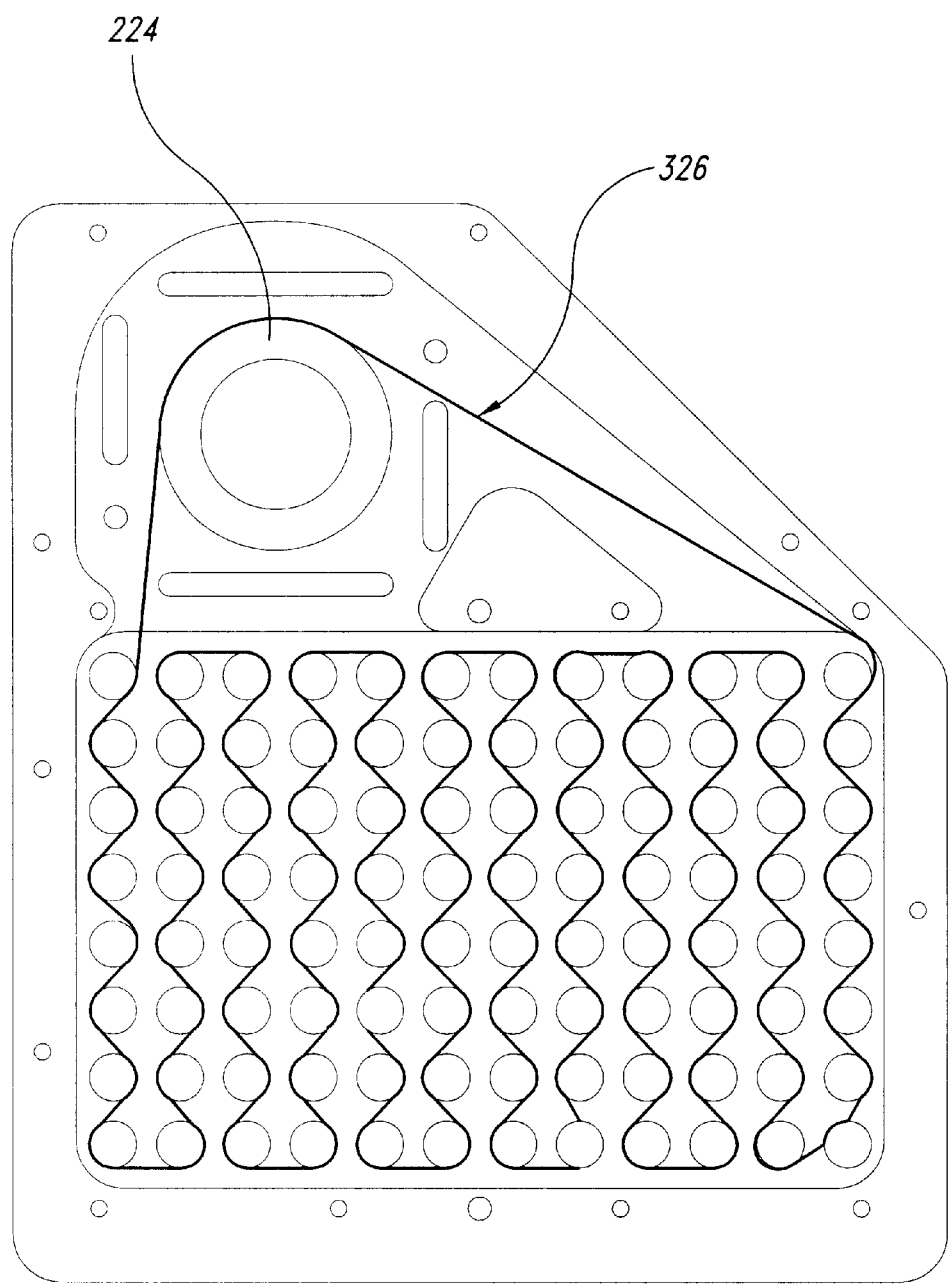
FIG. 3 is an overview of the microcentrifuge of FIG. 2 with an exaggerated belt for purposes of illustration.

FIG. 3 shows the path that a belt 326 takes around the pulley 224 and rotors 220. The belt 326 may be made from a variety of materials that tolerate temperature change and avoid stretching. Preferably the belt 326 is made of KAPTON polyimide tape (DuPont, Wilmington, Del.). In this configuration, the belt 326 is 61 inches in length, 0.250 inches wide and 0.003 inches thick. The belt 326 is held in place by a rotor "crown" (not shown) associated with the lower rotor (not shown), as discussed below. The belt 326 is further held in place by a pulley "crown" (not shown) associated with the pulley 224, which crown is a slight concave bulge with a radius of curvature of approximately 4.5 inches around the circumference of the outer surface of the pulley 224.

Figure 4A:
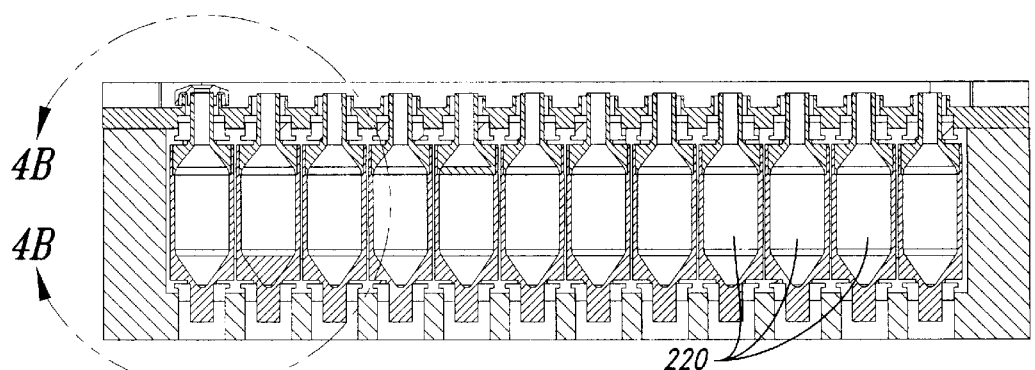
FIG. 4A is a cross-sectional view of a row of 12 centrifuge rotors.
Figure 4B:
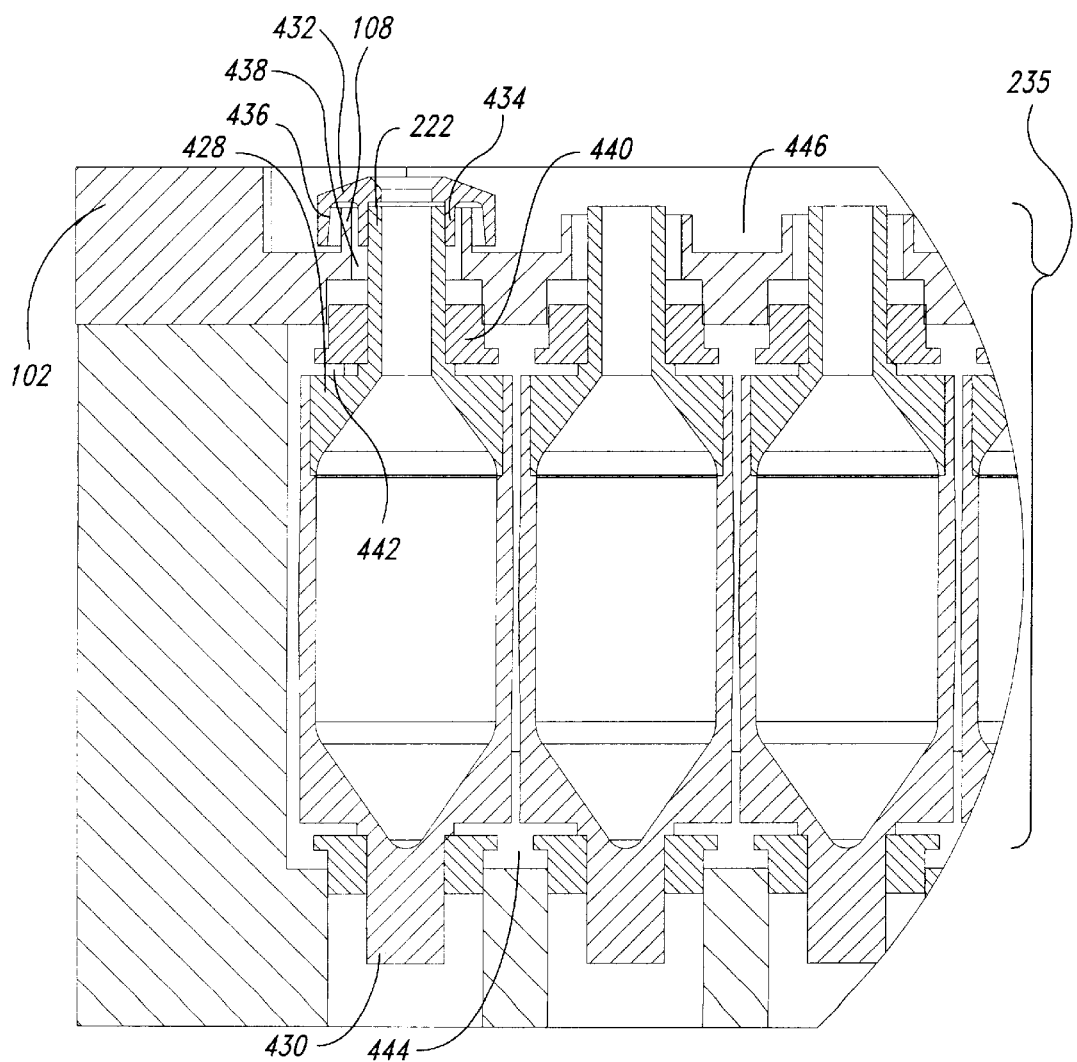
FIG. 4B is an enlargement of area B of FIG. 4A.

FIG. 4A is a cross section of twelve of the plurality of rotors 220. Circle "B" of FIG. 4A has been exploded in FIG. 4B. FIG. 4B shows the details of the assembly of each rotor 220, including the cooperation between rotors 220 and upper plate 102 (wherein a secure seal is formed that protects the inside of the microcentrifuge from fluid contamination and corrosion). Each of the plurality of rotors 220 may be fabricated in two parts: an upper rotor half 428 and a lower rotor half 430. The rotors 220 are further discussed below. The upper rotor half 428 includes the upwardly protruding shaft portion 222 (also shown in FIG. 2), wherein each shaft portion 222 is covered with a cap 432. The cap 432 is preferably made of TEFLON (DuPont, Wilmington, Del.). The cap 432 has an inner lip 434 and an outer lip 436. The inner lip 434 is flush with the upwardly protruding shaft portion 222 so as to form a tight seal. The outer lip 436 is positioned outside the raised cuff 108 of upper plate 102 and ends just above the upper plate 102, leaving a narrow space 438 (surface tension associated with a spilled fluid prevents any fluid from entering around the outside of the rotor).

Between upper plate 102 and upwardly protruding shaft portion 222 is a bearing 440, which presses on the shoulder 442 of upper rotor half 428 for controlled turning. Each bearing 440 is preferably lubricated and made of stainless steel, with a plastic retainer made of polyimide (DuPont, Wilmington, Del.). There may also be an optional O-ring 444 to absorb sound and to preload the bearings and decrease radial and axial movement. Each O-ring 444 is preferably made of silicone rubber. At location 446, outside the cap 432, an absorbent material (not shown) may also be placed to attenuate noise. Preferred is a sponge-like material or a fibrous mat with 96 holes or any other appropriate number cut out to accommodate the rotors 220, which can be easily removed and replaced.

Figure 5:
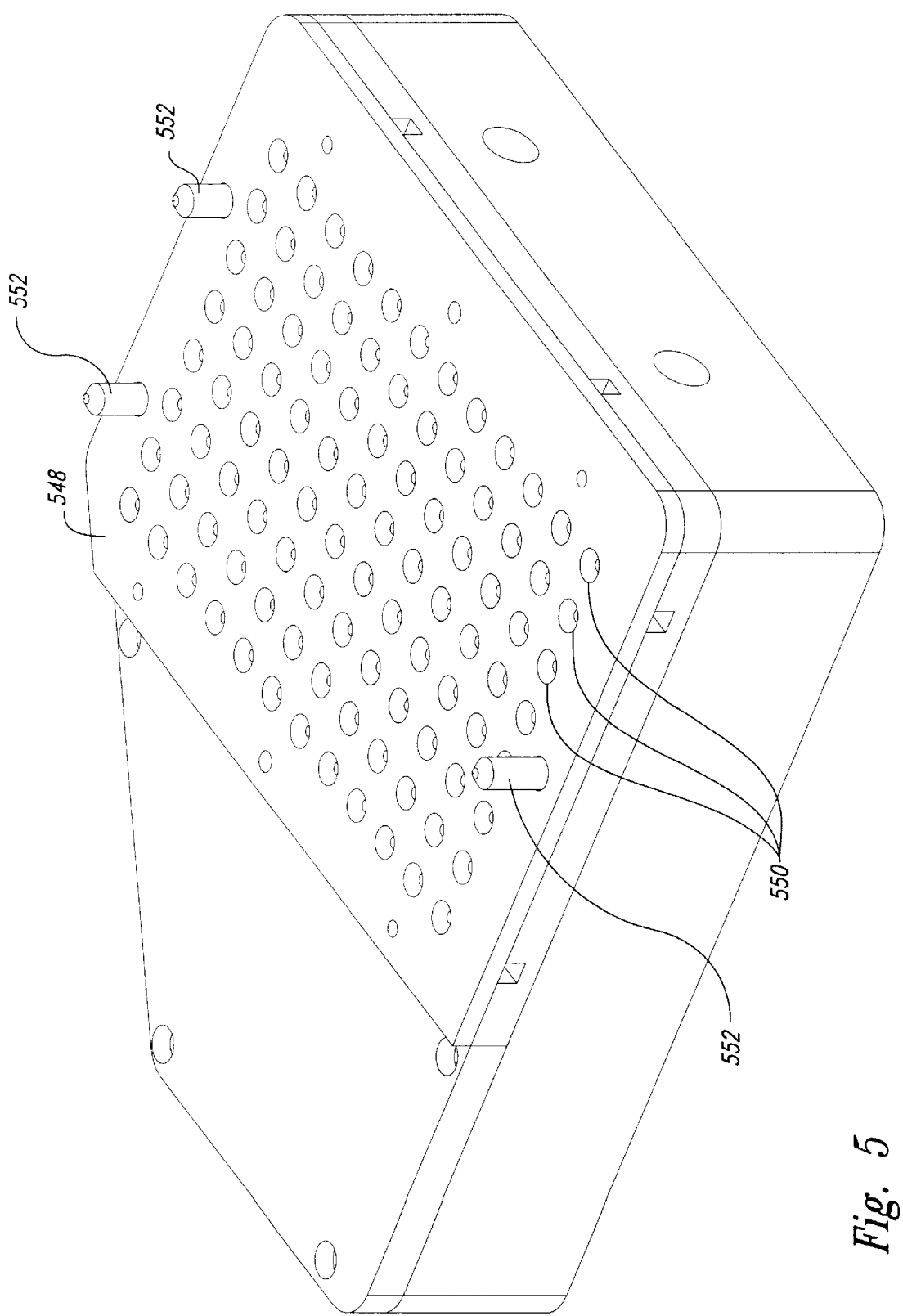
FIG. 5 is an overview of the top cover plate of the centrifuge that shows pins to align other tools.

FIG. 5 illustrates a top cover plate 548 having a plurality of sample inlet holes 550 to match up with the array of rotors (not shown). The top cover plate 548 holds the caps (not shown) in place during centrifugation. The top cover plate 548 is preferably made of a machinable plastic, such as a polycarbonate or acrylic plastic. Also illustrated are three alignment pins 552 that help align other instruments, such as for example a pipetter, with the plurality of sample inlet holes 550.

Figures 6A, 6B, 6C:
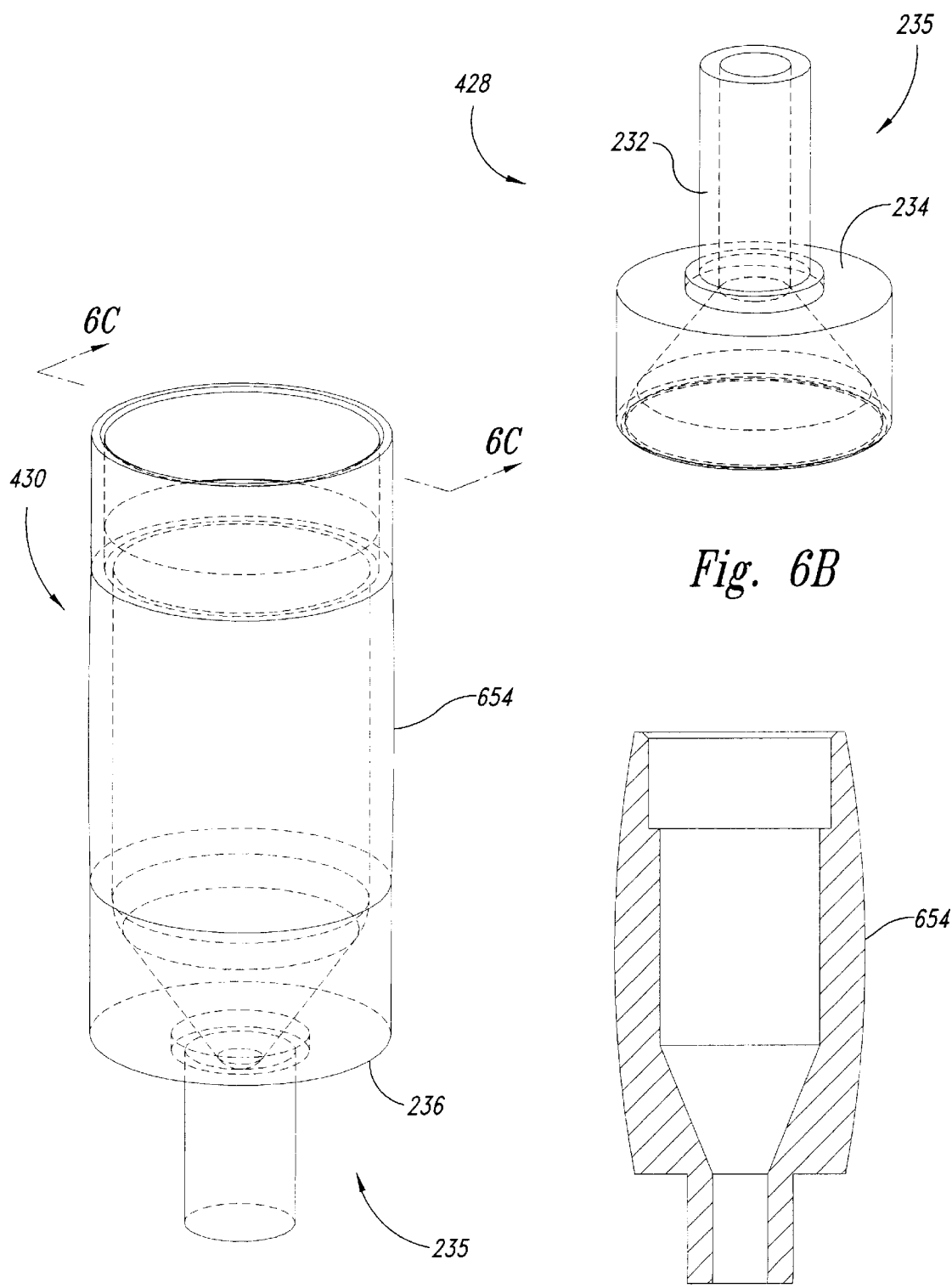
FIG. 6A shows the bottom half of the rotor.
FIG. 6B shows the top half of the rotor.
FIG. 6C is a cross-sectional view of FIG. 6A showing the slight bulge or crown of the bottom half of the rotor.

FIG. 6A, FIG. 6B, and FIG. 6C provide detail of the upper half 428 and the lower half 430 of each of the plurality of rotors, both outside and inside. Each rotor is preferably made from strong, non-reactive material such as titanium. On the lower half 430 and as best seen in FIGS. 6A and 6B, there is a "crown" 654, which constitutes a slight concave bulge with a radius of curvature of approximately 7 inches around the circumference of the outer surface of the rotor. The belt (not shown) seeks the highest point of the crown 654 such that the belt stays centered on the rotor and keeps it from sliding off its track.

Figure 7:
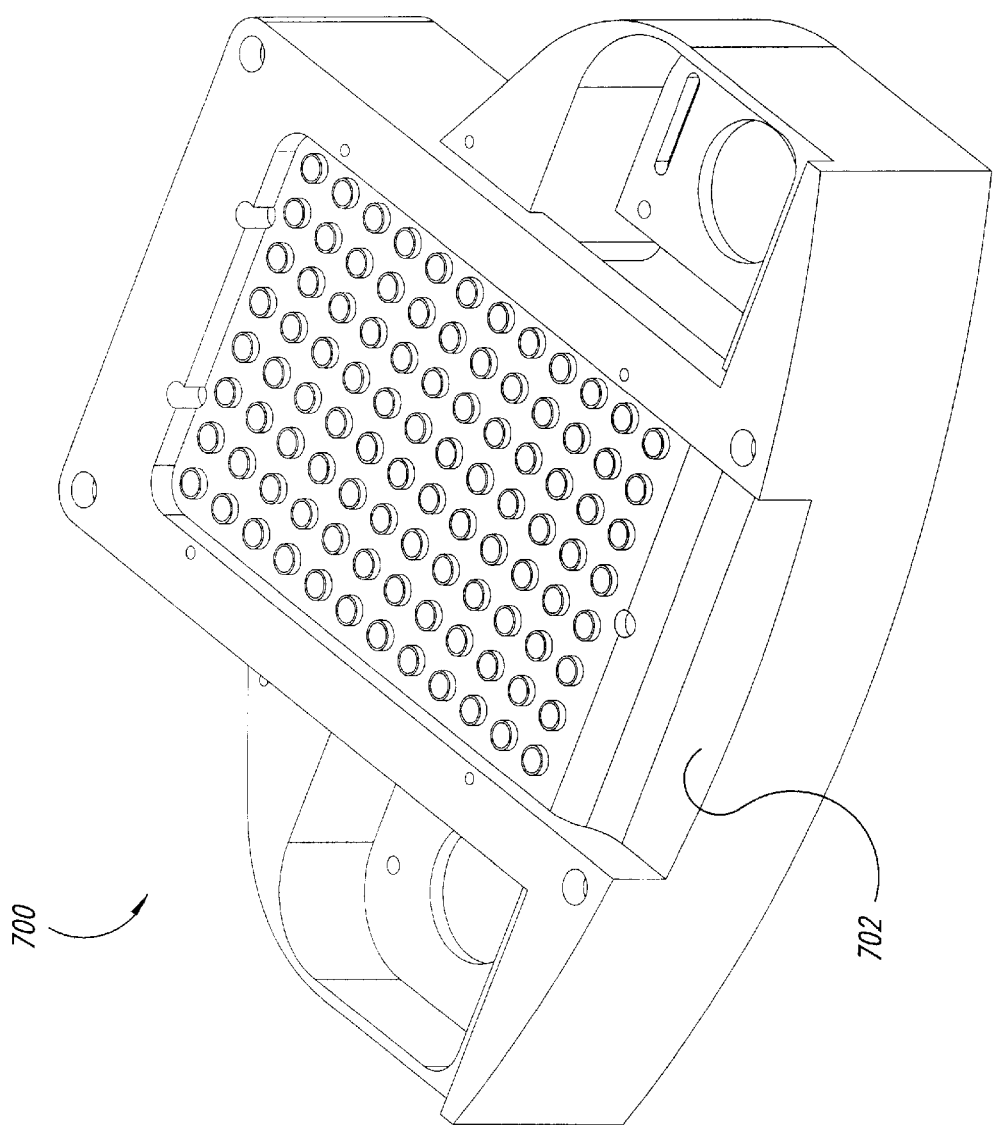
FIG. 7 illustrates a second embodiment of the microcentrifuge that can accommodate two motors.

FIG. 7 shows a top view of a second embodiment of the micro-array centrifuge of the present invention. In this configuration, the array centrifuge 700 has two motors (not shown). It is modular and can easily be moved to various desired locations in a workspace. In this embodiment there is no upper plate; rather the array centrifuge 700 includes an enclosure, preferably comprised of one piece. This solid configuration provides stability and sound abatement. FIG. 7 also illustrates a shelf 702 for spillage of the samples.

Figure 8:
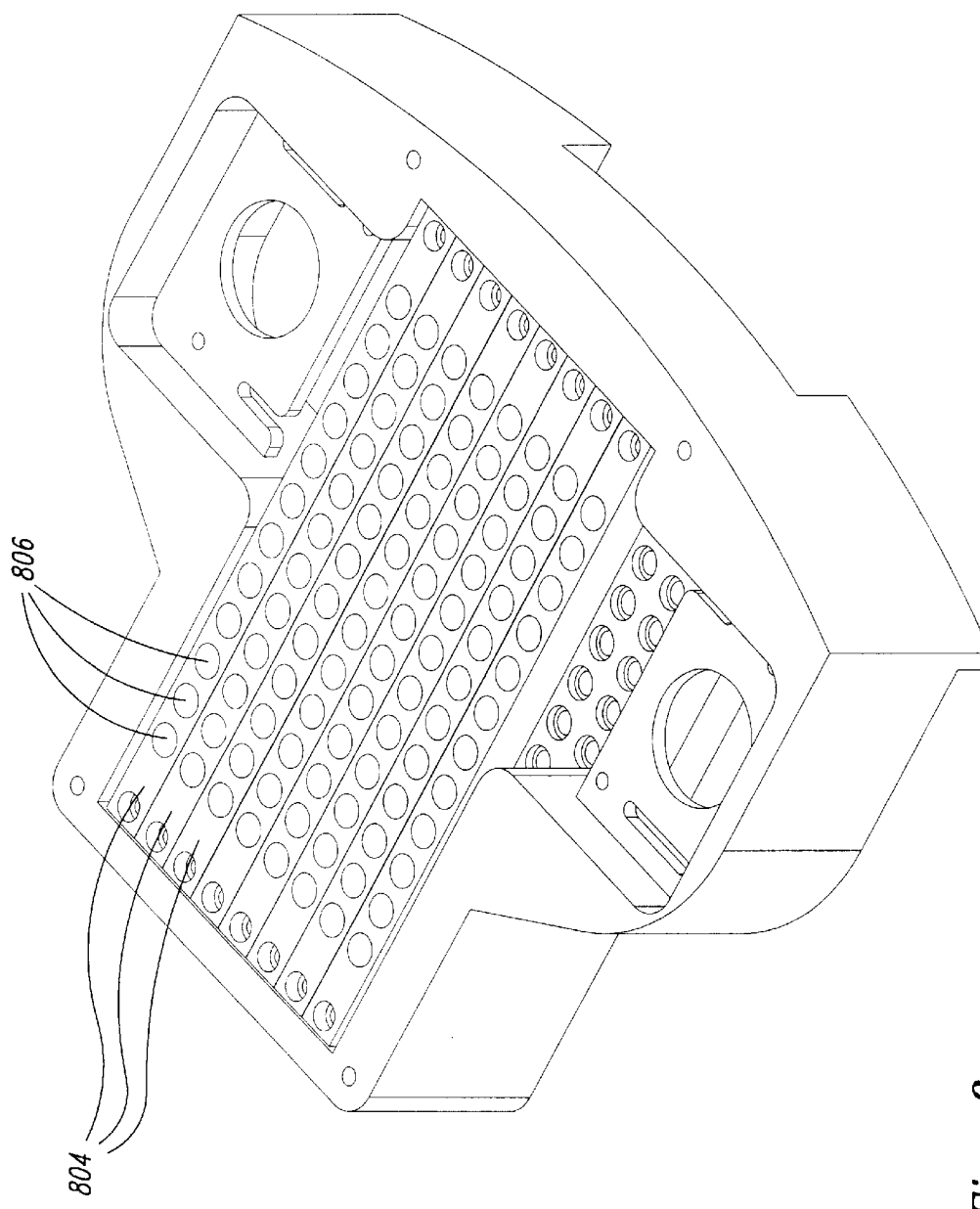
FIG. 8 illustrates the eight "strips" that comprise the lower plate of the second embodiment and can accommodate 12 rotors each.

FIG. 8 shows a bottom of the second embodiment, wherein the lower means for retaining the rotors (not shown) include 8 separate "strips" 804 that form a lower plate. Each strip 804 has a plurality of bottom holes 806 that hold 12 rotors (not shown) in place. Providing multiple strips significantly decreases the planar movement of the rotors that can occur in a solid lower plate that holds all 96 rotors. Each strip has end screw holes 808 for screws to securely anchor each strip.

Figure 9:
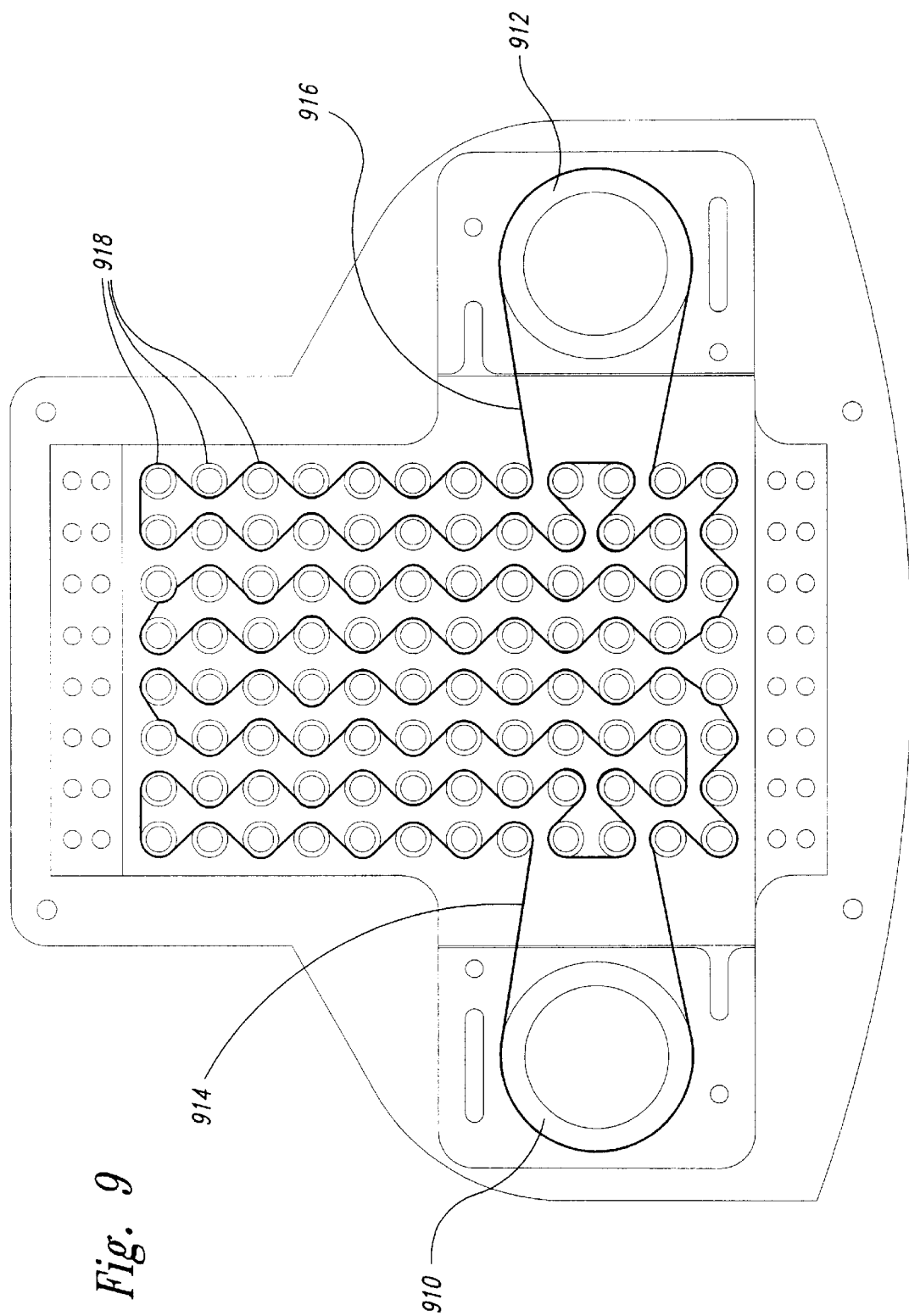
FIG. 9 highlights the path of two belts in the second embodiment of the microcentrifuge.

FIG. 9 illustrates how each of the two motors (not shown) associated with the second embodiment combine with two pulleys 910, 912 and two belts 914, 916 (each belt drives one half of the array). Each motor is connected to a remote computer (not shown) by a controller (also not shown), which determines when and how fast the rotors 918 will spin. The two belts 914, 916 are each weaved around its respective pulley 910, 912 and around one half of the plurality of rotors 918. The spinning of the pulleys 910, 912 moves the belts 914, 916 and in turn spins the array of rotors 918. The use of two motors lowers the power requirements of each motor thereby increasing their lives and centrifuge reliability. Moreover, in this second embodiment of the invention, the two belts 914, 916 each wraps around more surface area of its respective pulley 910, 912 (such differences in configuration may be observed by comparing FIGS. 9 and 3). The larger surface area results in a lower likelihood for belt slippage.

It can be seen that a 96-channel pipetter will work with the 96-well micro-array centrifuge. The advantages of the microcentrifuge are many. Because the rotors are so small, there is less mass to overcome in acceleration and deceleration. Hence, the rotors can accelerate rapidly to a speed of 2,000 revolutions and stop very quickly. The microcentrifuge takes up very little room and uses very little energy. Due to the small size and mass of the rotors, very high centrifugation forces can be achieved, on the order of 14,000 times the force of gravity and therefore very short sedimentation times can be obtained.

In another embodiment, various coatings, such as TEFLON or polypropylene, of the rotor interior provide optimal pellet retention and easy cleaning of the rotors.

In another embodiment of the microcentrifuge apparatus, the rotors are coupled to the source of motive power by a drive belt, wherein the source of motive power may be a motor or engine.

In another embodiment, the rotors are controlled by electromagnetic means. Each rotor effectively becomes an individual motor. A shaft is attached and extends out from the rotor. The shaft is surrounded by electrically conductive wire windings. A circular magnet surrounds these windings and is held in place by a retaining plate. The ends of the wire windings are attached to commutators. The commutators are contacted by electrically conductive metal brushes. Electrical current from the motor control source is supplied through the brushes to the windings to produce alternating magnetic fields. The interaction of this alternating magnetic field with the stationary circular magnet produces torque on the shaft that drives the circular rotation of the rotor. The same control voltage can be applied to all motors allowing all rotors to rotate at the same speed. Additionally, each motor can be controlled individually allowing each rotor to achieve different rotational speeds.

In another embodiment of the array centrifuge, the rotors are disposable. The use of disposable rotors avoids the problem of the cross-contamination of samples. The rotors fit into an independent drive train comprised of a plurality of permanent rotor encasements and a motive means. Each sample is processed in its own unique disposable rotor and is replaced before a new sample is introduced. This avoids the need for washing out the rotors between samples and saves processing time.

Figure 10:
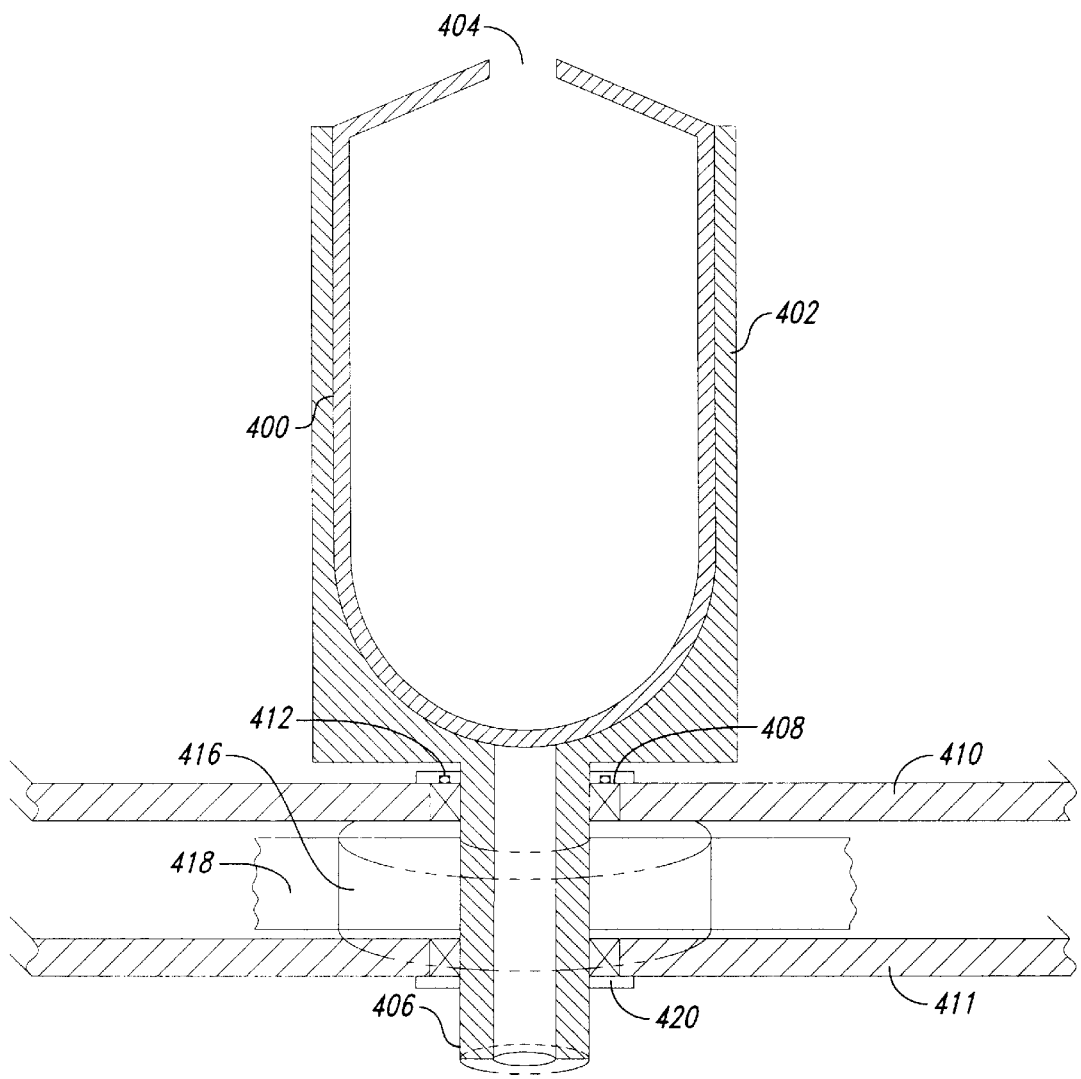
FIG. 10 is a partial cross-sectional view of a disposable rotor embodiment.

FIG. 10 illustrates the preferred embodiment of the apparatus with disposable rotors. The disposable rotors are preferably made of a tough non-reactive material such as polypropylene. Each disposable rotor 400 fits snugly into a rotor encasement 402 of the array centrifuge. The encasement is preferably made from strong material such as titanium. The rotor encasement 402 has at least one opening 404 into which a disposable rotor 400 may be inserted. The lower portion of the rotor encasement has a shaft 406 that fits into one or more bearings 408 that accommodate the movement of the rotor encasement 402. The bearings 408 are preferably lubricated and comprised of stainless steel, with a plastic retainer made of polyamide (DuPont, Wilmington, Del.). Each bearing 408 has at least one retaining plate 410 to hold the bearing 408 in place. There may also be an optional O-ring 412 between the lower portion of the rotor encasement 402 and the retaining plate 410 to absorb sound and preload the bearings 408 and decrease radial and axial movement. The O-rings 412 are preferably made of silicone rubber.

Directly below the first bearing 408, a pulley 416 is wrapped around the shaft 406 of the rotor encasement 402. A belt 418 may be woven around each pulley 416 in the array of rotor encasements 402 for motion. The belt 418 is actuated by a motive means, such as a motor (not shown) and an independent pulley (not shown). Beneath the pulley 416 is a second lubricated bearing 420 and at least one retaining plate 411 to keep the bearing 420 in place. Optionally, an O-ring 412 may be used to absorb sound and preload the bearings 420 and decrease radial and axial movement.

Figure 11A:
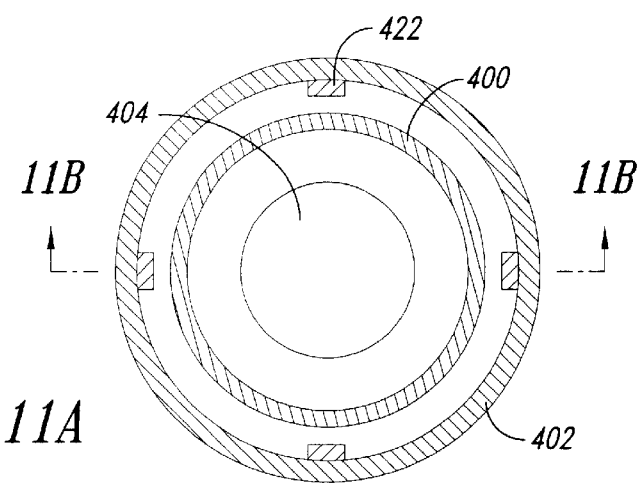
FIG. 11A is a top view of the disposable rotor with spacers.
Figure 11B:
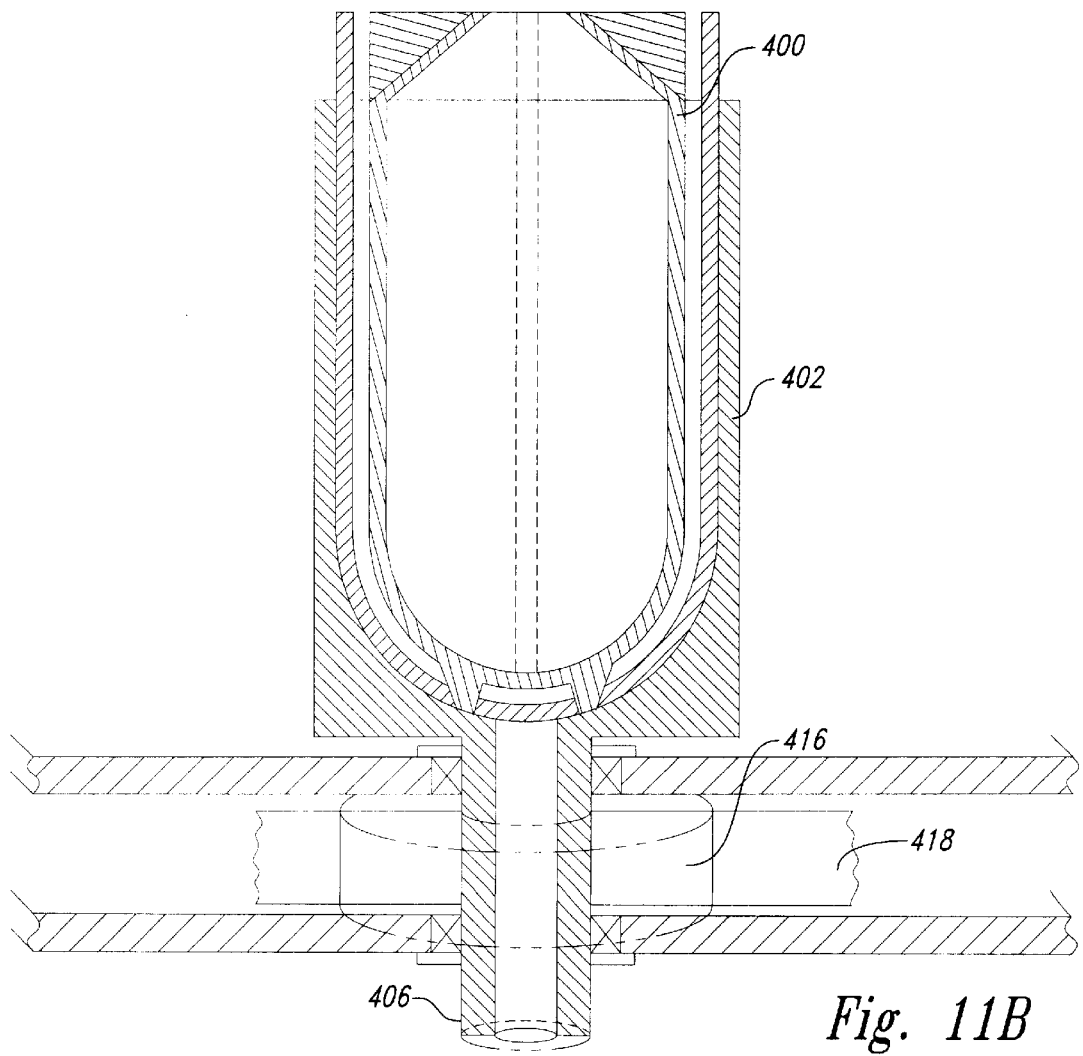
FIG. 11B is a cross-sectional view of the disposable rotors with spacers.

Figures 11A and 11B illustrates yet another embodiment of disposable rotors for an array centrifuge. The disposable rotor 400 includes spacers 422 on the outside of the rotor 400 as shown in FIG. 11 A. The spacers 422 maintain a pocket between the rotor 400 and the rotor encasement 402. FIG. 11B illustrates that the rotor 400 is shorter in length than the rotor encasement 402 which creates a space between the bottom of the rotor 400 and the rotor encasement 402. This design allows for spillage of the samples to drain down the sides of the rotor 400 and out the bottom of the shaft 406 to avoid sample contact with the mechanical parts of the apparatus. Sample contact with the mechanical parts of the apparatus, such as the belt 418 or pulley 416, could corrode parts.

In another embodiment of disposable rotors, the rotors have one or more chambers for the retention of samples. This embodiment of the rotor decreases the likelihood of cross-contamination in sample preparations. The chambers are stacked on top of one another inside the disposable rotor. Each chamber, for example, can contain a sample, a precipitation agent, a buffer, and a mixing reagent or other liquid necessary for a particular protocol. An entire cell preparation can be accomplished without the sample ever leaving the rotor's chamber.

For example, a rotor with a first chamber containing plasmid DNA and its host *E. coli* cells suspended in a growth media and a second chamber containing a precipitation agent could be used to isolate DNA. The rotor is centrifuged and a cell pellet containing the DNA forms on wall of the rotor. At the end of centrifugation, supernatant is collected at the bottom of the rotor. The supernatant is aspirated from the first chamber. A re-suspension reagent, a lysis buffer and a neutralization buffer are each added individually, mixed with the DNA and its host *E. coli* cells and centrifuged. After this process is completed, a pellet made up of flocculants, such as a cell membrane, mitochondria, and other cell organelles, is formed on the wall of the first chamber and plasmid DNA is dissolved in the lysate at the bottom of the chamber. Typically, the next step in the isolation of DNA is removing the lysate containing the plasmid DNA and replacing or cleaning out the rotors before the DNA is further purified. In this embodiment of rotors, the lower half of the first chamber is punctured, and the lysate containing the DNA flows through into the second chamber leaving the pelletted flocculants behind. The precipitation agent in the second chamber is then mixed with the lysate containing the plasmid DNA. The centrifuge is actuated and spins the rotor, forming a DNA pellet on the wall of the rotor. When the centrifuge is brought to a standstill, there is a DNA pellet on the wall and alcohol at the bottom of the rotor. The alcohol is removed. 70% ethanol is added to wash the DNA. The mixture of 70% ethanol and DNA is centrifuged and the excess ethanol is removed. Water is added and the DNA is resuspended in it. This process results in purified DNA suspended in water with less likelihood of cross-contamination of the samples.

EXAMPLE 1

Plasmid DNA Isolation

The disclosed array centrifuge can be used in conjunction with a robotic workstation for the automated isolation of plasmid DNA (RevPrep™, GeneMachines, San Carlos, Calif.). The workstation includes, but is not limited to, a bulk reagent dispenser, a 96-channel pipetter, a server arm and the disclosed array centrifuge. All tools are available from GeneMachines, San Carlos, Calif. The workstation has a base, a deck, and a support column. In this configuration, the bulk reagent dispenser and 96-channel pipetter are connected to the support column, on which they move vertically. The disclosed array centrifuge and a wash station are bolted to the rotary deck, and at least one microwell plate sits on the deck, which moves the items thereon horizontally to interact with the tools on the column. LabVIEW™ Software (National Instruments™, Austin, Tex.) is programmed to run this configuration of the robotic workstation.

Plasmid DNA and its host *E. coli* cells suspended in a growth media are contained in a plurality of wells of a microwell plate. The microwell plate is placed on the deck of robotic workstation by a robotic server arm. The deck moves horizontally until the microwell plate is precisely aligned with the pipetter. The pipetter is vertically moved toward the deck, and it aspirates the samples of growth media and cloned plasmid DNA from the microwell plate. The pipetter is then moved to its original position.

The array centrifuge is located on the deck of the robotic workstation. The deck moves horizontally until the array centrifuge is precisely aligned with the pipetter. The pipetter is vertically moved toward the array centrifuge and deposits the samples into a plurality of rotors of the array centrifuge. The pipetter is then moved back to its original location. The array centrifuge is actuated, and the rotational rate of the rotors is increased from a standstill position to a maximum rotational rate of around 60,000 rpm in 20 seconds. This rotational rate is maintained for approximately 30 to 40 seconds. During this time, the cell pellet, forms on the interior wall of the rotor, and the supernatant with the plasmids collects towards the center of the rotor. The rotational rate is steadily decreased to a standstill over a period of two minutes and the supernatant is collected at the bottom of the rotor. This length of time limits turbulence and accidental re-suspension of the cells. The pipetter is then vertically moved towards the array centrifuge, the supernatant is aspirated, and the pipetter vertically moves back to its original position.

The deck then moves horizontally until the array centrifuge is precisely aligned with the bulk reagent dispenser.

The dispenser moves vertically toward the array centrifuge and dispenses a resuspension reagent into the array of centrifuge rotors. The centrifuge rotors are rapidly accelerated and decelerated to resuspend the cells in the resuspension reagent. Twenty-five acceleration/deceleration cycles occur in as few as 20 seconds with the rotors approaching a top speed of about 20,000 rpm. Meanwhile, the bulk reagent dispenser has obtained and introduces Lysis buffer into the array of centrifuge rotors. The bulk reagent dispenser is then moved to its original position, while the rotors are then gently accelerated and decelerated to mix the re-suspended cells and the lysis buffer without disrupting the plasmid DNA, yet lysing cell membranes. The mixture is incubated for 3 to 5 minutes.

In the meantime, the bulk reagent dispenser has moved to the wash station where it rinses the pipette tips and aspirates neutralizing buffer. As the array centrifuge slows, it is moved to the pipetter, which dispenses neutralization buffer into the array of centrifuge rotors after it has come to a complete stop. The mixture is gently mixed by accelerating and decelerating the rotors and then incubated for 3 to 5 minutes. This brings the pH back to neutral before the plasmid DNA is denatured. The array centrifuge is actuated and the rotational rate of the rotors is increased from a standstill position to a maximum rotational rate of around 60,000 rpm in 20 seconds. This rotational rate is maintained for approximately 1 minute. The rotational rate is steadily decreased to a standstill over a period of two minutes.

A pellet forms on the interior wall of each centrifuge rotor and is made up of flocculants such as cell membranes, mitochondria, and other cellular organelles. Plasmid DNA dissolved in the lysate is located at the bottom of each rotor. Alcohol precipitation and centrifugation may further purify the plasmid DNA.

It is to be understood that the description above is intended to be illustrative and not restrictive. Many embodiments will be apparent to those of skill in the art upon reviewing the above description. The scope of the invention should be determined not with reference to the above description but should instead be determined with reference to the appended claims, along with the full scope of equivalents to which such claims are entitled.

While the invention has been described in some detail by way of illustration, the invention is amenable to various modification and alternative forms, and is not restricted to the specific embodiments set forth. These specific embodiments are not intended to limit the invention but, on the contrary, the intention is intended to cover all modifications, equivalents, and alternatives falling within the spirit and scope of the invention.

We claim:

1. A micro-array centrifuge comprising:
    a lower plate with a plurality of recesses;
    an upper plate with a plurality of holes, each hole lined by a raised cuff;
    a plurality of rotors, each having a longitudinal axis, top bottom, crown, side and an upper shaft, the side and crown maintaining contact with a drive belt;
    a cap with an inner and an outer lip, the inner lip adhering to the upper shaft and the outer lip being outside of the raised cuff and in close proximity to the top surface of the upper plate, whereby fluid is prevented from getting into the microarray centrifuge; and
    each rotor bottom contacting at least one bearing which contacts at least one of the plurality of recesses of the lower plate.

2. The microcentrifuge of claim 1, wherein the lower plate comprises a series of strips, each of which is anchored at its end.

3. A microcentrifuge apparatus adapted to simultaneously spin a plurality of samples, comprising:
    an upper plate having a plurality of upper plate holes
    a lower plate having a plurality of lower plate holes or recesses, wherein the lower plate is adjacent and substantially parallel to the upper plate, and wherein the plurality of lower plate holes or recesses are in axial alignment with the plurality of upper plate holes;
    a plurality of rotors for retaining and spinning the plurality of samples, wherein the plurality of rotors are positioned between the upper plate and the lower plate, and wherein each of the plurality of rotors has at opposing ends an upper shaft and a lower shaft, wherein the upper shaft of each of the plurality of rotors engages one of the upper plate holes and wherein the lower shaft of each of the plurality of rotors engages one of the lower plate holes or recesses such that the axes of rotation of each of the plurality rotors are substantially perpendicular to the upper and lower plates, and wherein each of the rotors has a central outer surface portion positioned between the upper and lower plates, wherein the central outer surface portion is outwardly bulged;
    a pulley, and
    a drive belt operatively engaged with the pulley and the central outer surface portion of each of the plurality of rotors.

4. The microcentrifuge apparatus of claim 3, wherein the outwardly bulged central outer surface portion of each rotor is concave.

* * * * *